United States Patent
Marlett et al.

(10) Patent No.: US 6,676,979 B2
(45) Date of Patent: Jan. 13, 2004

(54) UNFERMENTED GEL FRACTION FROM PSYLLIUM SEED HUSKS

(75) Inventors: Judith A. Marlett, Madison, WI (US); Milton H. Fischer, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 10 days.

(21) Appl. No.: 09/949,561

(22) Filed: Sep. 10, 2001

(65) Prior Publication Data

US 2002/0142054 A1 Oct. 3, 2002

Related U.S. Application Data

(62) Division of application No. 09/328,611, filed on Jun. 9, 1999, now Pat. No. 6,287,609.

(51) Int. Cl.$^7$ .................. A61K 35/78; A61K 31/715
(52) U.S. Cl. .................. 424/738; 424/725; 536/123; 536/128; 514/54
(58) Field of Search ................ 514/54; 536/123, 536/128; 424/738, 725

(56) References Cited

U.S. PATENT DOCUMENTS

| | | | |
|---|---|---|---|
| 5,234,916 A | 8/1993 | Hord | 514/57 |
| 5,248,502 A | 9/1993 | Ndife | 424/195.1 |
| 6,287,609 B1 | 9/2001 | Marlett et al. | 427/738 |

OTHER PUBLICATIONS

Cabotaje, L.M. et al., "Mucin secretion in germfree rats fed fiber–free and psyllium diets and bacterial mass and carbohydrate fermentation after colonization", *Appl. & Environ. Microbiology,* 1994, 60(4), 1302–1307.

Kennedy, J.F. "Structural data for the carbohydrate of ispaghula husk", *Carbohydrate Research,* 1979, 75, 265–274.

Laidlaw, R.A. et al., "Studies of seed mucilages. Part V. Examination of a polysaccharide extracted from the seeds of plantago ovata forsk by hot water", *Journal of the Chemical Society,* 1950, Part1, 528–534.

Marteau, P. et al., "Digestibility and bulking effect of ispaghula husks in healthy humans", *Gut,* 1994, 35, 1747–1752.

Sandhu, J.S. et al., "The gel nature and structure of the carbohydrate of ispaghula husk", *Carbohydrate Research,* 1981, 93, 247–259.

Laidlaw, R.A. et al., "Studies of seed mucilages.Part III. Examination of a polysaccharide extracted from the seeds of plantago ovata forsk", *Journal of the Chemical Society,* 1949, 1600–1608.

*Primary Examiner*—Francisco Prats
(74) *Attorney, Agent, or Firm*—Woodcock Washburn LLP

(57) ABSTRACT

A purified form of a gel-forming component of psyllium seed husks is disclosed, along with a process for obtaining the gel-forming fraction from psyllium seed husks. Methods of using this gel-forming fraction as a laxative and hypocholesterolemic agent are also disclosed.

8 Claims, No Drawings

UNFERMENTED GEL FRACTION FROM PSYLLIUM SEED HUSKS

This application is a divisional of U.S. application Ser. No. 09/328,611, filed Jun. 9, 1999, issued Sep. 11, 2001 as U.S. Pat. No. 6,287,609.

Pursuant to 35 U.S.C. §202(c), it is acknowledged that the U.S. Government has certain rights in the invention described herein, which was made in part with funds from the National Institutes of Health, Grant No. DK21712.

FIELD OF THE INVENTION

This invention relates to the field of laxatives, treatments to lower blood serum cholesterol and low-calorie food thickeners and fat substitutes. In particular, the invention relates to unfermented gel-forming polysaccharides from psyllium seed husks and methods for their isolation.

BACKGROUND OF THE INVENTION

Various scientific and scholarly articles are referred to in parentheses throughout the specification. These articles are incorporated by reference herein to describe the state of the art to which this invention pertains.

The seed husks of psyllium (*Plantago ovata*, also known as ispaghula) are commonly used as a laxative and to promote regular bowel function. Psyllium seed husks promote Taxation partially by increasing the mass and moisture content of the stool (Marteau et al., 1994, Gut 35:1747–1752). Additionally, the excreta of animals and humans fed diets containing psyllium seed husk is gelatinous. This gelatinous property contributes to laxative properties of psyllium seed husks by decreasing friction in the gut. Observed increases in fecal mass and water retention also have been attributed to this gelatinous material (Marteau et al., 1994, supra). The gel is composed largely of unfermented psyllium polysaccharides (Cabotaje et al., 1994, 1302–1307).

Currently used preparations of psyllium seed husks have certain disadvantages. Laxative preparations of psyllium seed husks are generally composed of ground husk and have coarse and unpleasant mouthfeel when administered in drinks. Psyllium seed husks have been incorporated into cookies, crackers and similar products; however, these products have a tendency to begin to gel unpleasantly in the mouth. More significantly, though, psyllium seed husks can swell in the esophagus, producing an esophageal obstruction that can cause choking. For this reason, psyllium seed husk preparations are not recommended for ingestion by persons who may have difficulty swallowing (e.g., elderly persons). Finally, the recommended daily dose of psyllium husk of 3.5–11 g per day is inconvenient to ingest in any form. What is needed is a form of psyllium husk that is convenient and pleasant to use.

Psyllium seed husk has many of the properties of soluble dietary fiber sources. Commonly used sources of soluble dietary fiber include pectin, gums and oat bran. Soluble dietary fiber (SDF) has many uses in food and medicinal preparations. Soluble fibers are components of minimally processed food sources such as oats, oat bran and barley, or are available as concentrates, such as gums, pectins and mucilages. Gums and mucilages are carbohydrate polymers that are generally isolated from plant sources. Mucilages in particular produce slippery or gelatinous solutions in water. Pectins are polymeric chains of partially methylated galacturonic acids that also possess the ability to form a gel in water. Most soluble fibers are rapidly and completely fermented and have no Taxation properties.

Sources of soluble dietary fiber that are also viscous lower serum cholesterol in animals and humans (Marlett, 1997, pp. 109–121, *Dietary Fiber and Health*, Plenum Press, New York, ed. Kritchevsky and Bonfield). The viscosity of the SDF, rather than its fermentation in the gastrointestinal tract, is key to its hypocholesterolemic action (Marlett et al., 1994, Hepatology 20:1450–1457). Viscosity in the lumen of the lower small intestine interferes with the absorption of bile acids and more bile acids are lost through the stool. Blood cholesterol is thought to be lowered primarily because it is being used in the liver to synthesize more bile acids to replace those lost. The synthesis of bile acids in the liver accounts for 40 to 50% of the daily elimination of cholesterol from the blood. However, the addition of one source of soluble fiber, oat bran, to the diet also increases the proportion of deoxycholic acid in the bile acid pool, which decreases the absorption of exogenous dietary cholesterol. Supplementing the diet with psyllium husk also increases the excretion of bile acids by about 50% (Gelissen et al., 1994, Am. J. Clin. Nutr. 59:395–400).

Soluble dietary fiber concentrates are also often used as thickeners and low calorie fat substitutes in the food industry because of their hydrocolloidal properties (Ward, 1997, Cereal Foods World, 42:386–390). Low-viscosity gums such as gum acacia have both hydrophilic and lipophilic properties that make them ideal as emulsifiers, surfactants and stabilizers. Pectins and mucilages have gel-forming properties that made them ideal thickeners of food products. Pectins are traditionally extracted from apple and citrus fruits. Commonly used mucilages are generally extracted from seaweed and include carrageenan, agar and alginate. A fat substitute can be made by combining gum with mucilage and/or pectin to create a compound with the emulsifying properties and smoothness of a fat.

SUMMARY OF THE INVENTION

The present invention provides the gel-forming component of psyllium seed husks in a purified form. This gel fraction provides the Taxation and hypocholesterolemic effects of intact psyllium seed husks, but is in a form that is easily administrable as a tablet, capsule or liquid, without certain unpleasant or unsafe qualities associated with the use of intact psyllium seed husks. The gel fraction also has utility in treatment of other intestinal abnormalities and maintaining normal bowel function, and as a food thickener and fat replacement.

According to one aspect of the invention, a gel-forming fraction of psyllium seed husks that survives microbial fermentation upon passage through a monogastric mammalian digestive tract is provided. Among other components, the gel fraction comprises predominantly xylose and arabinose in a dry weight ratio of at least about (preferably about 3.5). The fraction comprises notably limited amounts of other sugars, e.g., about 2.5%–13.5% total of rhamnose, galactose, glucose and uronic acids. More specifically, the gel-forming fraction has the following sugar composition, expressed as a percentage of total sugars:

between about 0.5% and 4% rhamnose;
between about 19% and 22% arabinose;
between about 68% and 76% xylose;
between about 0% and 0.5% mannose;
between about 1% and 2% galactose
between about 0% and 1% glucose; and
between about 1% and 6% uronic acids Upon further purification, the gel-forming fraction becomes even more depleted in rhamnose, glucose and uronic acids.

The gel-forming fraction is also highly viscous, a 0.2% concentration in formamide having an apparent viscosity of at least 500 sec, preferably 750 sec, and most preferably 850 sec. The fraction is soluble in a dilute alkaline solution and forms a gel upon acidification of the solution to a final pH of about 4.5.

According to another aspect of the invention, in a preferred method of obtaining the psyllium seed husk gel-forming fraction, a separate carbohydrate fraction is also obtained. This fraction is soluble in the dilute alkaline solution and remains soluble upon acidification of the solution to a pH of about 4.5. This fraction is comprised of xylose and arabinose in a ratio of at least about 4:1 and further comprises at least about 12% (by weight) rhamnose and at least about 15% (by weight) uronic acids.

According to another aspect of the invention, a method of fractionating psyllium seed husks to obtain a gel-forming fraction and an additional carbohydrate fraction is provided. The method comprises: (a) mixing the husks, in the presence of a chemical reducing agent, in an aqueous alkaline solution comprising between about 0.15 and about 1.0 M (preferably 0.15–0.5 M, more preferably 0.15–0.4 M, even more preferably 0.15–0.3 M and most preferably 0.15–0.2 M) hydroxyl ions, thereby fractionating the husks into an alkali soluble fraction and an alkali-insoluble fraction; (b) removing the alkali insoluble fraction; (c) acidifying the alkali soluble fraction to a pH of between about 3 and about 6 (preferably between about 4 and about 5, most preferably about 4.5), which results in the gelation of the gel-forming fraction; and (d) separating the gel fraction, e.g., by centrifugation, from the additional carbohydrate fraction contained in the acidified solution. In preferred embodiments, the method further comprises washing the gel fraction with an aqueous or buffered solution and desiccating the washed gel fraction.

In another aspect of the invention, a gel-forming fraction from psyllium seed husks is provided, which is produced by the aforementioned procedure. The additional carbohydrate fraction is also provided in this aspect of the invention.

According to another aspect of the invention, alternative methods are provided for obtaining a polysaccharide fraction that contains the aforementioned gel-forming fraction. Such a fraction is obtained by solvent extraction using formamide, dimethylsulfoxide or 4-methylmorpholine N-oxide (50% solution in water). The solvent-treated material is centrifuged to recover the soluble materials that are then poured into ethanol to achieve a concentration of 80% ethanol. The precipitate that forms is similar in composition to the alkali-soluble gel-forming fraction.

According to another aspect of the invention, pharmaceutical preparations for treatment of constipation or other intestinal abnormalities, or for lowering serum cholesterol levels in a patient are provided. These preparations are formulated to contain effective dosages of the psyllium seed husk gel-forming fraction of the invention. Methods of treating patients for these various conditions are also provided, which comprise administering the pharmaceutical preparations of the invention.

Other features and advantages of the present invention will become apparent from the detailed description and examples that follow.

DETAILED DESCRIPTION OF THE INVENTION

The present invention provides a highly polymerized gel-forming fraction from psyllium seed husks that has great utility in the treatment and prevention of constipation and as a hypocholesterolemic agent. This gel fraction remains substantially unfermented during transit through the gastrointestinal tract and promotes laxation through a variety of means, including increasing moisture content and overall mass of stool and imparting to the stool a slippery characteristic that facilitates ease of passage of stool (Example 6).

The gel-forming fraction from psyllium seed husks has also been demonstrated as a hypocholesterolemic agent. Accordingly, the gel-forming fraction may be used alone or in combination with other active substances as a therapeutic treatment to lower serum cholesterol.

Stool from rats and humans fed psyllium seed husks are sometimes gelatinous (Cabotaje et al., 1994, supra; Example 6). However, attempts to purify and characterize a gel-forming material (Kennedy et al., Carbohydrate Res. 75:265–274, 1979; Sandhu et al., Carbohydrate Res. 93:247–259, 1981) have not been successful and none has provided the highly purified gel-forming fraction having the features described in accordance with the present invention. The method of fractionating psyllium seed husks developed in accordance with the invention has led to the unexpected discovery, contrary to published reports (e.g., Kennedy et al., 1979, supra), that a gelatinous, alkali-soluble fraction of psyllium seed husks can be further fractionated to form a highly viscous gel fraction (referred to herein as "Fraction B") and a second carbohydrate fraction with distinctive compositional features, as described in greater detail below (referred to herein as "Fraction C"). Both the viscous, gel-forming Fraction B and the additional Fraction C are soluble in a variety of substances, including dilute and concentrated alkali, formamide, dimethysulfoxide and 4-methylmorpholine N-oxide (50% aqueous solution); consequently, these two fractions together can be isolated on the basis of these solubility characteristics. However, the further separation of the fractions has been either unsuccessful (e.g., a strong alkali-extracted gel-forming fraction was unable to be further separated by Kennedy et al., 1979; supra) or has remained unexplored. The present inventors have discovered that, using a suitable first extraction procedure to obtain a product comprising fractions B and C together, that the fractions can be separated by acidification of a solution containing a mixture of the fractions. Fraction B is concentrated for separation from the acidified mixture by centrifugation, whereas Fraction C remains soluble in the acid.

Description of Carbohydrate Polymers

The viscous, gel-forming psyllium seed husk fraction of the invention (Fraction B) is comprised primarily of xylose and arabinose. In a preferred embodiment, the gel-forming fraction has at least 50% xylose and arabinose by weight, in a more preferred embodiment at least 75% xylose and arabinose by weight, and in a most preferred embodiment at least 85% xylose and arabinose by weight. The gel-forming fraction has an apparent viscosity, as determined in the method of Example 3, of at least 500 sec, in a more preferred embodiment of at least 750 sec, and in a most preferred embodiment of at least 350 sec. The gel-forming fraction is furthermore particularly deficient in rhamnose, galactose and uronic acids, as compared to xylose. In a preferred embodiment, the ratio of weights of xylose to rhamnose is more than 50, in a more preferred embodiment the ratio is more than 60, and in a most preferred embodiment, the ratio is more than 65. In a preferred embodiment, the ratio of weights of xylose to galactose is more than 25, in a more preferred embodiment the ratio is more than 35, and in a most preferred embodiment, the ratio is more than 42. In a preferred embodiment, the ratio of weights of xylose to uronic acid is more than 15, in a more preferred embodiment the ratio is more than 25, and in a most preferred embodiment, the ratio is more than 35. In a preferred embodiment, the ratio of weights of xylose to arabinose of Fraction B is between 2.5 and 4.5, in a more preferred embodiment the ratio is between 3.0 and 4.0, and in a most preferred embodiment, the ratio is between 3.25 and 3.75.

The acid-soluble psyllium seed husk fraction (Fraction C) is also high in xylose and arabinose. In a preferred embodiment, the acid-soluble fraction has at least 25% xylose and arabinose by weight, in a more preferred embodiment at least 40% xylose and arabinose by weight, and in a most preferred embodiment at least 45% xylose and arabinose by weight. Though Fraction C has an apparent viscosity similar to that of fraction B, it does not have the gel-forming property of Fraction B. Fraction C is furthermore particularly enriched in rhamnose, galactose and uronic acids, as compared to xylose. In a preferred embodiment, the ratio of weights of xylose to rhamnose is less than 6.0, in a more preferred embodiment the ratio is less than 4.5, and in a most preferred embodiment, the ratio is less than 3.0. In a preferred embodiment, the ratio of weights of xylose to galactose is less than 40, in a more preferred embodiment the ratio is less than 30, and in a most preferred embodiment, the ratio is less than 25. In a preferred embodiment, the ratio of weights of xylose to uronic acid is less than 30, in a more preferred embodiment the ratio is less than 10, and in a most preferred embodiment, the ratio is less than 5.0 In a preferred embodiment, the ratio of weights of xylose to arabinose of Fraction C is more than 3.0, in a more preferred embodiment the ratio is more than 4.0, and in a most preferred embodiment, the ratio is more than 4.5.

Preparation of Psyllium Seed Husk Fractions

The present invention also provides methods of fractionating psyllium seed husks to yield the purified and separated fractions described above. In its most basic form, the method has the following steps:

1. Suspend psyllium seed husks in a dilute alkaline aqueous solution (preferably 0.15–0.2 M, hydroxyl ions) containing a reducing agent, in which portions of the husk material will dissolve, while a certain portion remains insoluble;

2. Remove the alkaline-insoluble material (referred to herein as "Fraction A"), e.g., by centrifugation;

3. Acidify the alkali-soluble fraction of step one to a pH of between 3 and 6, preferably 4.5, to yield a gel (Fraction B) and an acid-soluble fraction (Fraction C); and 4. Separate the gel from the acidified solution, e.g., by centrifugation.

One example of this method is taught in Example 1. Many variations exist to the method that will not substantially change the product isolated. These are described in detail below.

The alkaline solubilization step has several variations. The method taught in Example 1 has improved this solubilization over that found in the prior art. Previous alkaline solubilizations of psyllium seed husk polysaccharides utilized concentrated solutions of base (i.e. 1.2 M NaOH, Kennedy et al., 1979, supra) without a reducing agent. Recognizing the harsh nature of this treatment and its partial degradation of polysaccharide chains in the gel-forming fraction, the inventors have demonstrated that a gel-forming fraction can be obtained, presumably in a form more suitable for further fractionation, using a much less concentrated alkaline solution and a suitable chemical reducing agent, such as borohydride. Though up to 4 N alkaline solution can be utilized, the concentration of base in the alkaline solubilization is preferably at least 0.15 N and not more than 1.0 N; in a more preferred embodiment, at least 0.15 N and not more than 0.5 N; and in the most preferred embodiment, at least 0.15 N and not more than 0.2–0.3 N. Any standard base can be used in the alkaline extraction, including, but not limited to, sodium hydroxide, potassium hydroxide, lithium hydroxide, ammonium hydroxide and tetramethyl ammonium hydroxide.

A chemical reducing agent, such as borohydride, should be added to the alkaline solubilization step to minimize base-catalyzed depolymerization. In Example 1, a concentration of 1 g/L of sodium borohydride is used, but effective concentrations range from about 50 mg/L to 10 g/L. In a preferred embodiment, the sodium borohydride concentration is at least 100 mg/L and not more than 4 g/L, in a more preferred embodiment at least 500 mg/L and not more than 2 g/L, and in a most preferred embodiment, at least 800 mg/L and not more than 1.2 g/L. Other forms of borohydride also are suitable for use in this step, including but not limited to, lithium borohydride, potassium borohydride and sodium cyanoborohydride.

The degree of initial processing of psyllium seed husks may alter the alkaline solubilization in ways that will be well known to those skilled in the art. It is important that the husk material be processed so that it is in small pieces, in order to allow the viscous polysaccharides to be easily separated from the insoluble and fibrous materials of the cell walls. In Example 1, the psyllium seed husks are milled, but any process that pulverizes the plant material can be used, and these processes are well known in the art.

The ratio of seed husk material to alkaline solution can be important for efficient solubilization of the polysaccharide fractions. In Example 1, a ratio of 2 g psyllium seed husk is added to 400 ml of alkaline solution, but this ratio can be varied without appreciably affecting the solubilization. For instance, the ratio can be varied so as to add as little as about 0.1 g seed husks or as much as about 4 g seed husks to a 400 ml alkaline solution. Additionally, the time of solubilization can be varied to optimize the procedure (0.5 hr–24 hr) at a range of temperatures (4–50° C).

Step two of the method of the invention requires that the alkaline insoluble materials be separated from the alkaline soluble materials. In Example 1, centrifugation is employed to accomplish this objective. However, numerous variations and other procedures may be substituted without substantially changing the soluble materials isolated. One skilled in the art will know how to alter the time and force of the centrifugation to adapt the separation to different centrifuge rotors, plant materials and alkaline solutions. Other methods that will accomplish this separation are well known in the art. Some of these methods will be better suited to large scale use of the method of the invention. Separation methods of interest include, but are not limited to, flow-through centrifugation or filtration (with agitation). Example 1 further teaches washing the insoluble materials with the alkaline solution and re-separation to improve the yield of the alkaline soluble materials. This washing step is optional but can be used to advantage to improve yield.

Step three requires that the alkaline soluble materials of step two be subjected to acidification. In Example 1 this is accomplished by adding glacial acetic acid to the combined alkaline soluble materials until the pH is adjusted to 4.5. The range of pH used for this acid solubilization can be varied without substantial effect on the products. In a preferred embodiment, the pH is between 3 and 6, in a more preferred embodiment, the pH is between 4 and 5, and in a most preferred embodiment, the pH is about 4.5 as described in Example 1. The choice of acid is also subject to variation. Examples of acids suitable for use in this step are acetic, hydrochloric, sulfuric, oxalic, trichloroacetic and trifluoroacetic acids, among others. Here as in step one, the duration, temperature, etc. of the solubilization can be varied, but preferably is carried out at ambient temperature for about 2 hours.

Step four requires that the acid insoluble gel-like material (Fraction B) be separated from the acid soluble materials (Fraction C). Centrifugation is typically employed to accomplish this separation. An optional washing of the insoluble gel mass (e.g., with water, buffer or other suitable solvent) may also be performed to improve the efficiency of the separation.

Preparing Fraction B and Fraction C for storage and/or use may employ several procedures. The polysaccharide preparations of Fractions B and C may be used or stored hydrated. If stored in a hydrated form, preservatives or bacteriostatic agents may be added. Drying the polysaccharide preparations is particularly advantageous for use or storage. In a preferred embodiment, Fraction B and Fraction C are desiccated by treatment with 95% ethanol, washing with diethyl ether and drying. The fractions also may be desiccated with other solvents, such as methanol, acetone or isopropyl alcohol. Any standard dehydration method (e.g., evaporation, lyophilization) may be used to dry the fractions, provided the temperature is maintained at less than about 40° C.

III. Uses of Psyllium Seed Husk Fractions

The psyllium seed husk fractions of the invention have uses as therapeutic treatments. In this regard, the viscous, gel-forming fraction, Fraction B, has been demonstrated effective in promoting Taxation and also as a hypocholesterolemic agent. This material can be used alone or in combination with other active substances in therapeutic or prophylactic preparations for constipation, diarrhea and/or high serum cholesterol. Such preparations can incorporate the gel-forming fraction in pills, capsules or liquids to be administered by mouth. In a preferred embodiment, a dried form of the gel is formulated for convenient administration as a pill or capsule. The gel re-hydrates upon ingestion. The gel-forming preparations can additionally be incorporated into food products. Since the active polysaccharides have been isolated away from the other plant cell components by the method of the invention, they will not have the unpleasant mouthfeel or the necessity to administer large dosages associated with the psyllium seed husk preparations currently in use.

The unfermented gel-forming polysaccharide from psyllium seed husks is well-known for its laxative effects on the monogastric mammalian digestive tract. For an adult human, a suitable dosage of the gel-forming fraction in dry form is about 2 g, one to three times a day, to maintain bowel regularity and as a treatment for constipation.

As described in Example 4, the gel-forming fraction of psyllium seed husks has been demonstrated as a hypocholesterolemic agent. Accordingly, this fraction also may be used alone or in combination with other active substances as a therapeutic treatment to lower serum cholesterol. For an adult human, a suitable dosage of Fraction B in dry form is from about 3 g to about 7 g daily. The psyllium husk Fractions B and C of the invention can additionally be used as food additives. They may be used as thickeners, gel-formers and bulking agents in prepared foods. They may also be combined with other food additives to make fat mimetic systems. Because the polysaccharide preparations of the invention are partially non-digested, they will additionally be low calorie, serum cholestrol-lowering and laxation-promoting. The polysaccharide preparations of Fractions B and C can be used in many of the food products where gums and mucilages are currently used.

The following examples are provided to describe the invention in greater detail. They are intended to illustrate, not to limit, the invention.

EXAMPLE 1

Fractionation of Psyllium Seed Husks

Milled psyllium seed husks (2 g) were stirred with 0.2 N potassium hydroxide (400 ml) containing sodium borohydride (400 mg) in a nitrogen atmosphere for 90 minutes. The mixture was centrifuged for 20 minutes at 23,500×g. The supernatant was decanted from an insoluble fraction that had settled out in the centrifuge bottle. The insoluble fraction (designated "Fraction A") was stirred with fresh potassium hydroxide-sodium borohydride solution (100 ml) for an additional 15 minutes and re-centrifuged. The supernatants from both centrifugations were combined. The pH of the combined supernatants was adjusted to 4.5 with glacial acetic acid, with stirring, at ambient temperature, then centrifuged for 60 minutes at 25,500×g. The supernatant (Fraction C) was decanted from a gel mass (Fraction B) that had settled out in the centrifuge bottle. The gel was washed gently with water (50 ml) to remove adhering supernatant solution and this wash water was added to the supernatant. The gel fraction was desiccated by treatment with 95% ethanol and finally washed with diethyl ether and dried.

Prior to desiccating Fraction B, in some instances the fraction was further purified by repeating the alkaline solubilization and acidification steps described above. The gel was re-suspended in 0.2 N KOH, acidified to pH 4.5 and centrifuged to recover the gel.

EXAMPLE 2

Measurement of the Sugar Composition of Psyllium Seed Husk Fractions B and C

The respective sugar compositions of the gel fraction (Fraction B) and the acid soluble fraction (Fraction C) produced by the method set forth in Example 1 were determined. Results are shown in Table 1.

TABLE 1

Composition of psyllium seed husk fractions (dry wt).

|  | Psyllium Seed Husks (2 g) | Alkali Insoluble (Fraction A) | Alkali Soluble | |
| --- | --- | --- | --- | --- |
|  |  |  | Acid Insoluble (Fraction B) | Acid Soluble (Fraction C) |
| Yield (g) | — | 0.323 | 1.164 | 0.255 |
| Composition (% dry wt) |  |  |  |  |
| Rhamnose | 3.17 | 0.49 | 0.95 | 14.86 |
| Arabinose | 19.93 | 33.58 | 19.45 | 8.11 |
| Xylose | 49.15 | 3.16 | 67.20 | 38.79 |
| Mannose | 2.17 | 10.84 | 0.0 | 0.0 |
| Galactose | 3.83 | 12.86 | 1.59 | 1.89 |
| Glucose | 4.37 | 19.34 | 0.37 | 0.75 |
| Uronic Acids | 5.41 | 3.58 | 1.74 | 16.84 |
| Ratios of |  |  |  |  |

TABLE 1-continued

Composition of psyllium seed husk fractions (dry wt).

|  | Psyllium Seed Husks (2 g) | Alkali Soluble | | |
|---|---|---|---|---|
|  |  | Alkali Insoluble (Fraction A) | Acid Insoluble (Fraction B) | Acid Soluble (Fraction C) |
| % dry wts |  |  |  |  |
| Xylose/Rhamnose | 15.50 | 6.45 | 70.70 | 2.61 |
| Xylose/Arabinose | 2.47 | 0.094 | 3.46 | 4.78 |
| Xylose/Galactose | 12.83 | 0.25 | 42.26 | 20.52 |
| Xylose/Uronic Acids | 9.08 | 0.88 | 38.62 | 2.30 |

EXAMPLE 3

Measurement of the Viscosity of the Psyllium Seed Husk Gel-Forming Fraction

Apparent viscosity of the gel-forming fraction (Fraction B) of psyllium husk was determined. The solution for apparent viscosity determination was prepared by stirring overnight a 0.2% solution of the dry fraction in formamide. The solution was then heated with stirring to 70° C. over a 5 minute period, and stirred for 1 hour at ambient temperature. The apparent viscosity was measured using a pipet viscometer (Ostwald Dropping Pipet Viscometer, Cat. No. 13-695, Fisher Scientific, Pittsburgh, Pa.). The viscosity of the solution was measured three times and mean values determined.

TABLE 2

Apparent viscosity of psyllium seed husk Fraction B.

|  | Apparent Viscosity (sec) |
|---|---|
| Alkaline Soluble, Acid Insoluble Fraction (Fraction B) | 876 |
| Formamide (solvent only) | 303 |

EXAMPLE 4

Solvent Extraction of Psyllium Seed Husk Components

Psyllium seed husk components may also be obtained by extraction with various solvents. Such solvents include formamide, dimethylsulfoxide and 4-methylmorpholine N-oxide (50% solution in water).

Milled psyllium seed husk (2 g) was added in small portions to a selected solvent (200 ml) with stirring over 30–60 min. The mixture was stirred for two days, then centrifuged for 40 min at 27,000×g. The pelleted insoluble material was resuspended and stirred in additional solvent (50 ml) for 30 min, then re-centrifuged. The combined supernatants were added, with stirring, to 95% ethanol (5 volumes), bringing the final ethanol concentration to 80%. Methanol, isopropyl alcohol, acetone or similar solvents could be substituted for ethanol in this step. The precipitate was collected and washed with absolute ethanol, followed by diethyl ether, then dried.

The ethanol-insoluble precipitate that forms is similar in composition to the alkali-soluble material described in Examples 1–3. The sugar compositions of fractions obtained by the foregoing initial solvent extraction are shown in Table 3.

TABLE 3

Sugar compositions of fractions (% dry wt)

|  | Formamide | 4-Methyl-morpholine N-oxide | Dimethyl sulfoxide |
|---|---|---|---|
| Rhamnose | 3.03 | 3.25 | 0.48 |
| Arabinose | 18.95 | 16.54 | 17.38 |
| Xylose | 65.56 | 57.47 | 65.33 |
| Mannose | 0.05 | 0.0 | 0.12 |
| Galactose | 1.54 | 1.50 | 1.64 |
| Glucose | 0.21 | 0.22 | 0.34 |
| Uronic Acids | 4.30 | 4.69 | 0.94 |

EXAMPLE 5

Effect of Psyllium Seed Husks and Fractions Thereof on Reabsorption of Bile Acids from the Small Intestines of Rats One of the major sites for the hypocholesterolemic action of dietary fiber is in the lower small intestine (ileum), through its effect on bile acids. Bile acids function as emulsifiers in the small intestine to facilitate fat digestion and absorption. They are synthesized from cholesterol in the liver, stored in the gall bladder and secreted into the small intestine in response to eating. Bile acids are conserved through re-absorption in the ileum and recycling back to the liver through the blood. Food is digested and fluid absorbed as digesta moves distally in the intestine, such that in the lower third of the small bowel, the lumenal contents consist largely of indigestible material (i.e. fiber) and some fluid. It is now known that many of the viscous soluble fiber sources retain their viscosity during transit through the upper gastrointestinal tract, and essentially become concentrated in the lower gut. The soluble fiber effectively interferes with the re-absorption of bile acids in the ileum, the only site in the gut that has the necessary transport proteins for bile acids. Bile acids lost through stool are replaced by new synthesis in liver from blood cholesterol, which effectively lowers blood cholesterol levels.

Rats were surgically modified by removing the cecum and colon, and re-connecting the end of the ileum to the rectum. After a recovery period of 7–10 days, these animals secrete soft, formed material referred to as ileal excreta. Ileal excreta is preferred to stool for measuring the effect of a substance on absorption of bile acids, because bacterial transformation of bile acids in the large intestine can render up to half of them unidentifiable in stool.

Test meals were fed to groups of rats. Each meal was fed to four rats; the test meals contained 5% fiber as either (1) psyllium seed husk (PSH); (2) cellulose (as a control); or (3) the amount of a selected seed husk fraction (A, B or C), singly or combined, that would be present in 5% psyllium seed husks. The test meals also contained a non-absorbable marker so that the concentration of the marker in the ileal excreta could be used to calculate of the amount of the test meal that was present in the ileal excreta collected.

The results of the acute test meal study are shown in Table 4.

TABLE 4

Bile acids excreted after feeding test meals containing various soluble fibers.

| Test Meal | Bile acids excreted* ($\mu$mol/g test meal) |
|---|---|
| Cellulose | 8.32 ± 2.42 |
| Unmilled PSH | 18.41 ± 2.61 |
| Fraction A | 9.07 ± 2.75 |
| Fraction B | 16.08 ± 3.20 |
| Fraction C | 13.76 ± 2.71 |
| Combined A, B, C | 15.65 ± 1.37 |

Mean ± SEM, n = 4 rats

An increase in bile acids excreted indicates a concomitant decrease in bile acids re-absorbed into the blood. An agent that prevents re-absorption of bile acids into the blood from the ileum is considered to have hypocholesterolemic properties. The results above demonstrate the hypocholesterolemic properties of psyllium seed husks and, more notably, of the conveniently-administrable gel-forming fraction, Fraction B, which was essentially equivalent to intact psyllium seed husks in hypocholesterolemic effect.

EXAMPLE 6

The Unfermented Gel Component of Psyllium Seed Husks Promotes Laxation as a Lubricant in Humans In addition to increasing stool weight, a supplement of psyllium seed husks (PSH) produces a stool that is slick and gelatinous. In this example, we demonstrate that a gel fraction of psyllium escapes microbial fermentation and is responsible for these characteristics that enhance Taxation.

Materials and Methods:

Experimental design. The study consisted of 3 periods, a screening phase, the PSH period and the basal period. During the screening phase, subjects consumed 15 g/d of Metamucil® (5 g/meal) (Smooth Texture Metamucil®, The Procter & Gamble Co., Cincinnati, Ohio), along with their usual diet, for 12 days to provide an additional 8.8 g/d of dietary fiber. Subjects were asked to complete food intake records during d 9–12 to evaluate compliance with a protocol and to obtain more information about typical food intakes. Two stools were obtained from each subject during d 9–12 also to evaluate compliance with the protocol. During the next 7 days (d 13–19 of the study), subjects consumed a defined, low fiber diet, and with each meal, the PSH and a nonabsorbable marker (chromic sesquioxide, 200 mg/meal). For the next two weeks (d 20–33 of the study), subjects consumed their usual diet to allow all of the PSH to be excreted. For the 7 days (d 34–40 of the study) of the basal phase, the same controlled, low fiber diet and nonabsorbable marker, but no PSH supplement, were consumed. This experimental design was based on results of a preliminary study. It was observed in the preliminary study that 7–10 d of ingesting the supplement were necessary to achieve a high level of PSH excretion. Preliminary observations also revealed that it took 7–10 d from ingestion of the last test dose for all of the PSH to be excreted. Therefore, the PSH period for data collection followed the 12 d of PSH consumption that constituted the screening phase and a crossover experimental design was not employed.

Stools and qualitative bowel response, food intake and activity data were collected daily during both weeks of controlled diet. This study was approved by the College of Agricultural and Life Sciences Human Subjects Committee, University of Wisconsin-Madison.

Subjects. Twenty-one of the 33 individuals who responded to local advertisements were enrolled in the screening phase. Criteria for exclusion from the screening phase were: lactose intolerance, non-omnivorous diet and unwillingness to follow a specified diet. Subject compliance, reliability, availability and attitude were evaluated during the screening phase, and 15 subjects (8 males and 7 females) were selected to participate in the study. Fourteen subjects completed the study. (Data from one subject who admitted to not providing all stools during the specified collection periods were deleted from the final analysis.) Subjects ranged in age from 18–30 yr (mean±SE, 24±1 yr) and were of normal body weight for height (body mass index, 24.2±0.9).

Diet. All subjects consumed fixed diets during the PSH-supplemented and basal phases consisting of foods provided to them as part of the study. Breakfast was consumed at home and consisted of Rice Krispies® cereal, skim milk, orange juice, white bread, margarine or butter, and jelly. Lunch consisted of a sandwich, fresh fruit, and milk. The evening meal consisted of a meat, a starch source, salad and dessert. Subjects consumed prescribed amounts of the menu foods. The amounts of bread and milk varied with daily energy needs. Limited amounts of fiber-free snacks and alcohol also were permitted. Coffee was allowed ad libitum. Subjects were supervised at the evening meal. Consumption of the supplement and nonabsorbable marker was verified daily when empty packets were exchanged for the next day's allotment of supplement.

Data and Sample Collection. All stools excreted during the PSH and basal phases of the study were individually collected, refrigerated promptly, and weighed and frozen within 8 h of collection. Subjects evaluated each stool using a 9 point rating scale consisting of: –4 disagree the most, –3 disagree extremely, –2 disagree very much, –1 disagree, 0 neutral, +1 agree, +2 agree very much, +3 agree extremely, and +4 agree the most possible.

Subjects completed daily food intake records to verify consumption of the items in the controlled diet. Physical activity forms were completed daily to identify any major changes in daily routine. Daily routines for each participant remained consistent throughout the two weeks of sample collection.

Analyses. Stools excreted during d 4–8 of each controlled diet period (d 16–20 and d 37–41 of the study) were thawed, pooled for each subject by hand mixing and re-frozen until use or processed as outlined below. Duplicate aliquots (3 g) were dried (16 h, 70° C.) to determine moisture content (Marlett et al., JNCI 76: 1065–1070, 1986). Stool chromium content was determined using a modification (Hosig et al., Cereal Chem. 73: 392–398, 1996) of the method of Guncaga et al. (Clin. Chim. Acta 47: 77–81, 1974). Portions of pooled stool were lyophilized for duplicate (25 mg) determinations of neutral and amino sugar content by gas chromatography as the alditol acetate derivatives after acid hydrolysis and reduction (Kraus et al., J. Chromatog. 513: 71–81, 1990; Monsma et al., Appl. Environ. Microbiol. 58: 3330–3336, 1992) and for uronic acid analysis using a colorimetric assay (Blumenkranz et al., Anal. Biochem. 54: 484–489, 1973). An aqueous extract of thawed, pooled stool was used to determine the relative viscosity of stool (Ostwald dropping pipet viscometer, Cat. No. 13-695, Fisher Scientific, Pittsburgh, Pa.). Aqueous fractions were obtained by vortexing aliquots (2 g) with water (10 ml), centrifuging (30, 000×g, 30 min, 4° C.), and recovering and re-centrifuging the supernatant.

The fractionation procedure to isolate the component responsible for the gel characteristic was applied to thawed aliquots of pooled stool from each subject from both diet periods. Aliquots (25 g) were de-lipidated and subjected to base (0.18 N KOH) containing sodium borohydride (0.026 M) to minimize base-catalyzed depolymerization. The alkali soluble fraction was acidified to pH 4.5 with glacial acetic acid and a precipitate (Fraction 1) recovered by addition to ethanol. Fraction 1 was suspended in water, heated to boiling, centrifuged and the supernatant reduced in volume by roto-evaporation. The concentrate was added to ethanol to give a final alcohol concentration of 70%. The fibrous mass which formed by addition of the concentrated supernatant to ethanol was washed with ethanol, ether and vacuum dried. This material represented the gelatinous component of PSH stools (Fraction 2). No precipitate formed at this point during the analysis of the control stool samples. Neutral and amino sugar contents and uronic acid concentrations were determined on aliquots of this material, as outlined above.

Macronutrient and energy contents of the planned menus and of the daily intakes of each subject were calculated using nutrient composition tables. Dietary fiber intakes were calculated from food intake records using a detailed database of the fiber content and composition for US foods. The sums of the daily intakes on d 2–6 of each controlled diet period (d 14–18 and d 35–39) were used as the intake of the neutral sugars (glucose, arabinose, xylose, mannose, galactose) and the uronic acids for the determination of apparent digestibility of fiber-derived sugars. The sugar composition of the PSH supplement also was measured by gas chromatography after acid hydrolysis, as outlined above. Fecal excretion of sugars was adjusted to reflect excretion of 5 d of intake using the content of chromium in the pooled stool (Chen et al., Am. J. Clin. Nutr. 68: 711–719, 1998). Apparent digestibilities of fiber-derived sugars were calculated as the difference between intake and excretion, and expressed as a percentage of intake (Chen et al., 1998, supra).

Statistical Analyses. Data are reported as the mean±SE. Data collected during the basal and psyllium-supplemented phases of the study were compared by one-way analysis of variance using SAS computer program software release 6.12. Significant differences were identified by the least significant difference means separation test.

Results:

The first fraction (Fraction 1) recovered by the gel isolation scheme was extracted from both basal and PSH-containing stools; this alkali-soluble fraction from PSH stools was significantly larger ($P<0.0005$) than that extracted from basal excreta. An ethanol-precipitable fraction (Fraction 2) that was gelatinous was extracted by hot aqueous treatment of the alkali soluble fraction from stool of subjects consuming the psyllium supplement. No gelatinous fraction was extracted from stool collected during the basal, low fiber phase of the study.

The major component in Fraction 2 isolated from stool of the 14 subjects consuming PSH was a polysaccharide that contained 763±18 mg of sugar/g of Fraction 2, most of which was xylose (64±1%) and arabinose (27±0%); the remainder of the sugars was (%) 2 glucose, 3 galactose, and 3 other sugars (fucose, ribose, mannose, myoinositol, muramic acid, glucosamine and galactosamine). The xylose and arabinose in this gel fraction accounted for 53.9±2.1 and 31.1±1.4% of the respective sugar in feces.

Since no fraction was obtained from basal excreta comparable to the gel isolated from the PSH-containing stool, aqueous extracts of stool were prepared for a comparison of the relative viscosity of stool from the two study periods. The apparent viscosity of the aqueous extract of the PSH-containing stool was significantly greater ($p<0.01$) than that of the basal, low fiber excreta, 238±38 vs 128±7 sec.

The PSH supplement increased mean daily wet output from 117±7 to 188±13 g/d ($P<0.0001$), mean daily dry output from 29±2 to 37±2 g/d ($P<0.0001$), and stool moisture from 74.4±0.9% to 80.2±1.0% ($P<0.05$). Other measures of large bowel function also were significantly different. The mean wet weight of each stool increased from 121±6 to 173±14 g ($P<0.005$), mean dry weight of each stool from 30±2 to 34±3 g ($P<0.0001$), and defecation frequency from 1.0±0.1 to 1.1±0.1 ($P<0.05$) when PSH supplement was consumed.

The mixed food controlled diet contained a mixture of fiber-derived sugars and the apparent digestibility of the fiber-derived total neutral sugars was 67±4% during the low fiber basal period. The composition of the PSH preparation was (mg/g): 21 rhamnose, 127 arabinose, 325 xylose, 8 mannose, 25 galactose, 44 glucose, 35 uronic acids, 19 ash, 18 crude protein and 346 coating. Apparent digestibilities of the fiber-derived xylose and arabinose decreased ($P<0.001$), while uronic acid digestibility increased ($P<0.03$) when the supplement was ingested. Subtracting xylose and arabinose excreted during the basal diet period from the amounts of these sugars in the PSH-containing stool provides a means of estimating the apparent digestibility of the two major sugars in PSH. The apparent digestibilities of the xylose, arabinose and total neutral sugars provided by PSH were 59±5, 28±7 and 54±9%, respectively and were variable.

The test dose of PSH was well tolerated by all subjects. Compared to large bowel function during the basal period, PSH resulted in gentler bowel movements, softer stools that were easier to pass, greater ease of wiping, a feeling a complete relief, and increased bulk. The PSH supplement had no effect on abdominal cramping, an urge to defecate, or experience a repeat bowel evacuation, nor did it cause diarrhea, although subjects perceived more flatulence and bloating. Although soft and formed, most stools were visibly gelatinous and would vibrate when agitated. The macronutrient and dietary fiber contents provided by the foods in the diet did not change when the PSH supplement was consumed.

Thus, in contrast to other viscous fibers that are completely fermented in the colon, a component of psyllium is not fermented. The results of the foregoing study indicate that, by functioning as an emollient and a lubricant, the unfermented gel isolated from PSH-containing stool represents a new mechanism of Taxation for a dietary fiber.

The present invention is not limited to the embodiments described and exemplified above, but is capable of variation and modification without departure from the scope of the appended claims.

We claim:

1. A method of fractionating psyllium seed husks to obtain a gel fraction and an additional carbohydrate fraction, the method comprising:

(a) mixing the husks in an aqueous alkaline solution comprising a base, wherein if the base comprises hydroxyl ions, the hydroxyl ions are present at a concentration of between about 0.15 and 1.0 M, thereby fractioning the husks into an alkali-soluble fraction and an alkali-insoluble fraction;

(b) removing the alkali-insoluble fraction;

(c) acidifying the alkali-soluble fraction to a pH of between about 3 and 6, thereby obtaining a an acid-insoluble gel fraction, and an acid-soluble fraction comprising the additional carbohydrate; and (d) separating the gel fraction from the solution containing the additional carbohydrate fraction.

2. The method of claim 1, wherein the husks are mixed in an aqueous alkaline solution comprising between about 0.15 and 0.3 M hydroxyl ions.

3. The method of claim 1, wherein the alkali soluble fraction is acidified to a pH of about 4.5.

4. The method of claim 1, which further comprises washing the gel fraction with an aqueous solution.

5. The method of claim 4, which further comprises desiccating the washed gel fraction.

6. The method of claim 1 wherein the mixing step further comprises a chemical reducing agent.

7. The method of claim 6 wherein the chemical reducing agent comprises a borohydride.

8. The method of claim 7 wherein the borohydride is sodium borohydride, lithium borohydride, potassium borohydride or sodium cyanoborohydride.

* * * * *